United States Patent
Luizzi et al.

(10) Patent No.: US 12,336,788 B2
(45) Date of Patent: Jun. 24, 2025

(54) METHODS AND SYSTEMS FOR FACILITATING DIAGNOSING OF A CENTRAL OR PERIPHERAL VASCULATURE DISORDER USING INTRAVASCULAR IMAGING

(71) Applicants: Brian Donald Luizzi, Fort Myers, FL (US); Philip Luizzi, Cape Coral, FL (US); Joseph G Magnant, Fort Myers, FL (US); Christopher James Luizzi, Fort Myers, FL (US); Chris Duca, Cape Coral, FL (US)

(72) Inventors: Brian Donald Luizzi, Fort Myers, FL (US); Philip Luizzi, Cape Coral, FL (US); Joseph G Magnant, Fort Myers, FL (US); Christopher James Luizzi, Fort Myers, FL (US); Chris Duca, Cape Coral, FL (US)

(*) Notice: Subject to any disclaimer, the term of this patent is extended or adjusted under 35 U.S.C. 154(b) by 192 days.

(21) Appl. No.: 18/453,149

(22) Filed: Aug. 21, 2023

(65) Prior Publication Data
US 2024/0041330 A1 Feb. 8, 2024

Related U.S. Application Data

(63) Continuation-in-part of application No. 16/691,237, filed on Nov. 21, 2019, now abandoned.
(Continued)

(51) Int. Cl.
*G06T 7/00* (2017.01)
*A61B 5/02* (2006.01)
(Continued)

(52) U.S. Cl.
CPC .......... *A61B 5/02007* (2013.01); *A61B 5/026* (2013.01); *G06T 5/50* (2013.01);
(Continued)

(58) Field of Classification Search
CPC ........ G06T 2207/30101; G06T 7/0012; G06T 2207/30104; G06T 17/00;
(Continued)

(56) References Cited

U.S. PATENT DOCUMENTS

| 5,453,575 A | 9/1995 | O'Donnell et al. |
| 7,397,935 B2 | 7/2008 | Kimmel et al. |

(Continued)

FOREIGN PATENT DOCUMENTS

| CN | 112997215 A | 6/2021 |
| CN | 115861132 A | 3/2023 |

OTHER PUBLICATIONS

Maso Talou, Gonzalo D et al. "Mechanical Characterization of the Vessel Wall by Data Assimilation of Intravascular Ultrasound Studies." Frontiers in physiology vol. 9 292. Mar. 28, 2018, https://www.nobi.nim.nih.gov/pmc/articles/PMC5882902/.
(Continued)

*Primary Examiner* — Hau H Nguyen

(57) ABSTRACT

Disclosed herein is a method of facilitating diagnosing of a vasculature disorder using intravascular imaging, in accordance with some embodiments. Accordingly, the method may include a step of generating, using an intravascular imaging device, at least one intravascular image associated with a patient. Further, the method may include a step of analyzing, using a processing device, the at least one intravascular image. Further, the method may include a step of determining, using the processing device, at least one vein diagnosis based on the analyzing. Further, the method may include a step of displaying, using a display device, the at least one vein diagnosis. Further, the method may include a step of storing, using a storage device, the at least one vein diagnosis and the at least one intravascular image associated with the at least one vein diagnosis in a database. In other embodiments, an artificial intelligence unit may be config-
(Continued)

ured to reconstruct missing data in at least one intravascular image and determine a value associated with the at least one intravascular image.

20 Claims, 14 Drawing Sheets

Related U.S. Application Data

(60) Provisional application No. 62/770,606, filed on Nov. 21, 2018.

(51) Int. Cl.
*A61B 5/026* (2006.01)
*G06T 5/50* (2006.01)
*G06T 17/00* (2006.01)
*G06V 10/25* (2022.01)
*G06V 20/50* (2022.01)

(52) U.S. Cl.
CPC ............ *G06T 7/0016* (2013.01); *G06T 17/00* (2013.01); *G06V 10/25* (2022.01); *G06V 20/50* (2022.01); *G06T 2200/04* (2013.01); *G06T 2207/20216* (2013.01); *G06T 2207/20221* (2013.01); *G06T 2207/30104* (2013.01); *G06V 2201/03* (2022.01)

(58) Field of Classification Search
CPC . G06T 2207/20081; G06T 2207/20084; G06T 2200/04; G06T 2207/30004; G06T 7/00; A61B 6/504; A61B 8/0891
See application file for complete search history.

(56) References Cited

U.S. PATENT DOCUMENTS

| | | |
|---|---|---|
| 7,940,969 B2 | 5/2011 | Nair et al. |
| 9,017,263 B2 | 4/2015 | Lerman et al. |
| 9,943,233 B2 | 4/2018 | Lavi et al. |
| 11,122,981 B2 | 9/2021 | Olender et al. |
| 2007/0016046 A1 | 1/2007 | Mozayeni et al. |
| 2016/0157802 A1 | 6/2016 | Anderson |
| 2020/0395126 A1 | 12/2020 | Walker et al. |
| 2020/0405269 A1 | 12/2020 | Swisher et al. |
| 2022/0296205 A1 | 9/2022 | Kang et al. |

OTHER PUBLICATIONS

Chen, Xingxin, et al., Deep-learning-based motion-correction algorithm in optical resolution photoacoustic microscopy, Visual Computing for Industry, Biomedicine, and Art, 2019, vol. 2, No. 12, <URL: https://doi.org/10.1186/s42492-019-0022-9>.
Yong, Yan Ling, et al., Linear-regression convolutional neural network for fully automated coronary lumen segmentation in intravascular optical coherence tomography, Journal of Biomedical Optics, 2017, vol. 22, No. 12, <URL: doi: 10.1117/1.JBO.22.12.126005>.

METHODS AND SYSTEMS FOR FACILITATING DIAGNOSING OF A CENTRAL OR PERIPHERAL VASCULATURE DISORDER USING INTRAVASCULAR IMAGING

FIELD OF THE INVENTION

Generally, the present disclosure relates to the field of data processing. More specifically, the present disclosure relates to methods and systems for facilitating a central or peripheral vasculature disorder using intravascular imaging.

BACKGROUND OF THE INVENTION

Vasculature disorders has been ignored by medical professionals. Further, upon labeling the vasculature disorders as low concern and hard to diagnose, vasculature disorder (or disease) cases may be untreated that may lead patients to serious health circumstances. Further, the vasculature disorders may include central vasculature disorders and peripheral vasculature disorders. Medical professionals may be slowly adopting the philosophy that vasculature disorders may be a problem worth intervening. Further, the vasculature disorders are only recently being taught as a concern at most medical schools. Further, the concerns for the vasculature disorders may be projected to grow exponentially with the increasing focus on the vasculature disorders.

Existing techniques for facilitating diagnosing of a vasculature disorder are deficient with regard to several aspects. For instance, current technologies diagnose the vasculature disorder by comparing cross-sectional area of a compressed vein with a standard reference. For, instance, the current technologies make use of a decision-making model that is deficient in measuring the cross-sectional area of the compressed vein. Further, the decision-making model is subjective, anatomic, and non-physiologic.

Further, in many instances, medical images, such as intravascular ultrasound (IVUS) images, may contain artifacts or missing data. There exists a need for an efficient, automated system to detect and repair missing data from IVUS images to improve the quality of the images to assist a professional in rendering a diagnosis. It is further desirable to be able to efficiently extract a value from intravascular images—such as a minimal cross sectional area of a vein.

Therefore, there is a need for improved methods and systems for facilitating diagnosing of a central or peripheral vasculature disorder using intravascular imaging that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is a method of facilitating diagnosing of a vasculature disorder using intravascular imaging, in accordance with some embodiments. Accordingly, the method may include a step of generating, using an intravascular imaging device, at least one intravascular image associated with a patient. Further, the method may include a step of analyzing, using a processing device, the at least one intravascular image. Further, the method may include a step of determining, using the processing device, at least one vein diagnosis based on the analyzing. Further, the method may include a step of displaying, using a display device, the at least one vein diagnosis. Further, the method may include a step of storing, using a storage device, the at least one vein diagnosis and the at least one intravascular image associated with the at least one vein diagnosis in a database.

Further disclosed herein is a system for facilitating diagnosing of a vasculature disorder using intravascular imaging, in accordance with some embodiments. Accordingly, the system may include an intravascular imaging device configured for generating at least one intravascular image associated with a patient. Further, the system may include a processing device communicatively coupled with the intravascular imaging device. Further, the processing device may be configured for analyzing the at least one intravascular image. Further, the processing device may be configured for determining at least one vein diagnosis based on the analyzing. Further, the system may include a display device communicatively coupled with the intravascular imaging device. Further, the display device may be configured for displaying the at least one vein diagnosis. Further, the system may include a storage device communicatively coupled with the processing device. Further, the storage device may be configured for storing the at least one vein diagnosis and the at least one intravascular image associated with the at least one vein diagnosis in a database.

Further disclosed is the inclusion of an artificial intelligence unit for facilitating accurate and efficient processing of any intravascular images. The artificial intelligence unit may be adapted to identify missing data, repair missing data, determine a value from a medical image, identify confluences, and determine at least one vein diagnosis based on the medical image.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION

Figure 1:
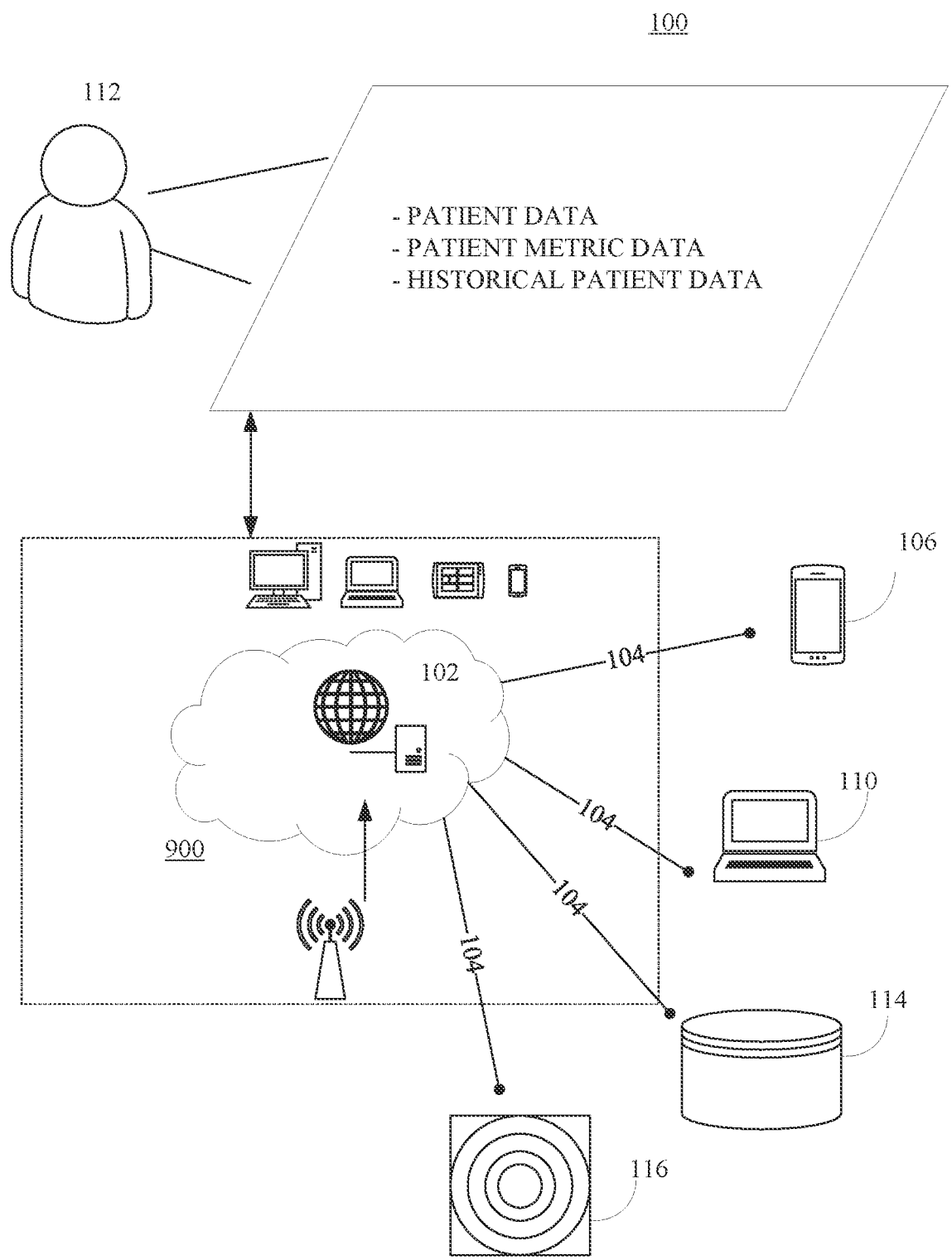
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of methods and systems for facilitating diagnosing of a central or peripheral vasculature disorder using intravascular imaging, embodiments of the present disclosure are not limited to use only in this context. It should be understood that, for the purposes of the written description, any reference to "intravascular imaging" or "IVUS images" or "IVUS frames" should be construed to include any similar medical imaging, including but not limited to: MRI imaging, x-ray imaging, ultrasound imaging generally, or any other similar medical procedures for producing visual images that are well-known in the art. It should be further understood that any reference to a "frame" should be construed to mean one image selected from one or more images from the same set of medical images. As a non-binding example, an IVUS procedure taken over three seconds may produce 90 frames of data at a rate of 30 frames per second, each frame corresponding to a single image taken from within that IVUS procedure.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor and at least one actuator. Examples of the one or more client devices and/or the server computer may include, a desktop computer, a laptop computer, a tablet computer, a personal digital assistant, a portable electronic device, a wearable computer, a smart phone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice based interface, gesture based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, it should be well understood that any reference to an "artificial intelligence unit" should be construed to describe a device that is both configured to communicate with any external device, and containing any computing hardware necessary to implement any artificial intelligence system well-known in the art, such as a neural network, machine learning system, or similar artificial intelligence system. Any reference to "training" the artificial intelligence unit should be understood to refer to the process of using existing data to teach an artificial intelligence good values and biases, as is well-known in the art. Unless stated otherwise, it should be understood that any computer system recited in this disclosure is capable of communication over a network using any communication component or components that are well-known in the art. Further, the server computer may include a communication device configured for communicating with one or more external devices. The one or more external devices may include, for example, but are not limited to, a client device, a third party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data finger-printing, role based access control, and so on.

Further, one or more steps of the method disclosed herein may be initiated, maintained, controlled and/or terminated based on a control input received from one or more devices operated by one or more users such as, for example, but not limited to, an end user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human readable secret data (e.g. username, password, passphrase, PIN, secret question, secret answer etc.) and/or possession of a machine readable secret data (e.g. encryption key, decryption key, bar codes, etc.) and/or or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smart-card with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview:

The present disclosure may describe methods and systems to facilitate diagnosing of a vasculature disorder using intravascular imaging. Further, the vasculature disorder may include a central vasculature disorder and a peripheral vasculature disorder. Further, the present disclosure may describe methods and systems for quantifying venous flow changes using intravascular images. Further, intravascular images may include intravascular ultrasound (IVUS) images. Further, the present disclosure may be designated for the treatment of Pelvic Venous Compression (PVC) cases associated with the vasculature disorder. Further, pelvic congestion syndrome (PCS) associated with the Pelvic Venous Compression (PVC) was brought into the spotlight with the identification of May-Thurner Syndrome. Further, the May-Thurner syndrome is a rarely diagnosed condition in which patients may develop deep venous thrombosis (DVT) due to an anatomical variant in which the right common iliac artery overlies and compresses the left common iliac vein against the lumbar spine. Further, the anatomical variant may be present in over 20% of the population. Further, until recent advancements with Intravascular Ultrasound (IVUS), PCS has been extremely difficult to diagnose and treat. Couple this with the inexperience of vein surgeons treating venous disease; it has left surgeons with a completely subjective viewpoint of treating the PCS disease. Further, the disclosed methods and systems may accomplish a plurality of goals. Further, the plurality of goals may include identification of the prevalence of the disease, generation/creation of an objective standard for when to intervene, fortification of the importance of venous disease diagnosis, and laying credible evidence to bring in late adopters (expand the market). Further, the venous disease/disorder is the inadequate function of the vein (weakened or defective valves) or the inadequate flow of blood through the vein (blockages or venous compressions). Venous Disease can be broken down into three main categories: Venous Insufficiency (VI), Venous Thromboembolic (DVT/PE), and Pelvic Venous Compression (Iliac vein compression syndrome, pelvic venous congestion—PCS). Venous Insufficiency is the most common form of Venous Disease and is usually superficial and treatable. Venous Thromboembolic conditions such as DVT are the most urgent. Until recent advancements of imaging devices, Pelvic Venous Compression has been rarely considered. According to Thomas Wright, M.D., FACP, RVT, Medical Director of Laser Lip & Vein Center in St. Louis, MO, "Untreated venous issues can lead to a multitude of serious health problems, including variceal bleeding, venous ulcers, and blood clots, also known as deep venous thrombosis. It's important to dispel the myth that Venous Insufficiency is just a cosmetic issue. Leaving venous issues untreated can eventually lead to much larger problems." Further, it may be a surprise to know that venous disease treatment is not a specialty taught in medical school. In the mid-1990s vein specialists taught themselves and then each other. Further, with the lack of awareness that many specialists may have not acknowledged that a venous disease may be a serious health concern. According to Deepak Sudheendra, MD, FSIR, RPVI, Vascular Interventional Radiologist, "As a physician, I can honestly say that I did not learn anything about Venous Disease in medical school. It was not discussed! Imagine every medical student in the country going off to practice medicine with little to no knowledge of Venous Disease!"

Further, the present disclosure may describe methods and systems to facilitate the detection and quantification of the severity of venous disease from Intravascular Ultrasound (IVUS) images. Further, upon using proprietary algorithms and calculations, the disclosed system may filter raw data received by the IVUS machine and convert the raw data into an objective evaluation that may identify the need for whether or not to intervene. Further, the disclosed methods and system mays fortify the importance of the Venous Disease diagnosis with quantifiable patient outcome reports that may be collected using the above mentioned objectified standards. Further, with the efforts of the previously laid out goals, our product will then be able to lay credible evidence to bring in late adopters (medical specialists) and expand the market.

Further, the disclosed methods and systems may relate to treating venous diseases, and more particularly to cases concerning Pelvic Venous Compression. Further, treating Pelvic Venous Compression currently depends on subjective decision making. Further, without a standard for interpreting the images obtained using IVUS; this subjective decision-making may lead to various interpretations regarding the severity of the disease, and more specifically whether or not to intervene and to what extent of intervention.

Further, the present disclosure may describe methods and systems that may solve the problem of interpreting the images by providing a quantifiable and qualitative physiological analysis of the patient's anatomical conditions including the identification and isolation of the problem (blockage, compression, lesion, thrombosis), and providing the surgeon with therapeutic decision making assistance.

According to some embodiments, the disclosed methods and systems enables setting a standard for intervention, an objective means of interpreting the IVUS image, increased confidence for intervention, a more efficient treatment strategy for the patient, and is a tool that will be used for the further evaluation and research of varying venous/cardiovascular diseases.

Further, the disclosed methods and systems may be utilized by interventionalists, surgeons, community and university hospitals, stent manufacturers, insurance companies, researchers, statisticians, and so on. Further, the surgeons may be the obvious users of this product. The initial intent is the use within the operating room as a therapeutic decision-making device designed to aid the surgeon with an objective reasoning of whether or not to intervene. Further, the second market may be hospitals. Hospitals may benefit from the use of the product as a result of better logging of treatment efficacy. Further, the disclosed methods and systems may lessen the likelihood of return patients. Further, the third market may be universities. Further, the universities may perform additional studies that may further strengthen evidence of the prevalence of this disease. Further, the fourth market may be stent manufacturers. Further, through efforts of objectified diagnosis, and improved patient outcomes, late adopters may broaden the market of this procedure and as a result—increase the need for the use of stents. Further, the fifth and sixth markets may be Insurance companies and researchers & statisticians. Further, the disclosed methods and systems may set up a nationwide (to be global) database of case studies. Further, documenting the evidence of a need for intervention, and identifying a prevalent demographic may result in better patient care.

Further, over 30 million Americans may be suffering from venous diseases and only 10 percent seek treatment, according to society for Vascular Medicine. Further, according to the Vascular Disease Foundation, a large U.S. survey, the Framingham study, reported that 27 percent of the American adult population had some form of venous disease in their legs. Further, through the efforts and the education of late adopters to venous diseases, patients suffering from venous diseases may greatly rise. Further, a plurality of medical specialists may accept the prevalence of the patients suffering from forms of venous disease. Further, the plurality of medical specialists may include orthopedics, dermatology, obstetrics and gynecology, wounds care doctors, urologists, neurology/sleep doctors, and so on. Further, the forms of venous disease may include ortho venous disease, dermato venous disease, Pelvic Congestion Syndrome (PCS), venous origin ulcer, night-time urination, Restless Leg Syndrome (RLS) and leg cramps, and so on. According to the Society for Vascular Surgery, chronic venous diseases may affect up to 40% of the U.S population. This percentage of the population may refer to the number of patients with chronic venous disease going untreated. Further, the disclosed methods and systems may begin to attract the late adopters and increase the number of diagnosed patients with any form of chronic venous disease to an estimated 130,280,000.

Further, the disclosed system may use existing anatomic data recorded from Ultrasound Images to calculate physiologic data and detect a presence of venous compression that may be used to make objective clinical decisions regarding whether to intervene and to what degree. Further, the present disclosure may describe methods and systems that may include automated lumen measurements, proprietary image filtering methods, statistical and probability analysis for diagnosis and treatment. Further, the disclosed system may be handled as a "black box" attachment to the main imaging machine.

Further, the disclosed methods and systems may facilitate the expression of iliac vein compression lesions in terms of physiologic flow reduction. Further, the disclosed methods and systems may facilitate expression of Iliac vein stent results in terms of physiologic flow improvement. Further, the disclosed methods and systems may assist the operator in deciding when to intervene to determine how much improvement. Further, the disclosed methods and systems may assist the operator in deciding when to intervene to determine if a need to intervene further, or what future steps to take in the patient's treatment. Further, the disclosed methods and systems may create an objective standard of when to intervene.

According to some embodiments, the disclosed methods and systems may facilitate the identification of prevalence of Pelvic Venous Compression disease and fortify the importance of venous disease diagnosis. Further, the disclosed methods and systems may facilitate establishment of credible evidence for the necessity of the procedure versus a non Intravascular Ultrasound (IVUS) procedure. Further, the disclosed methods and systems may begin with raw data collected from the Intravascular Ultrasound (IVUS) machine. Further, the raw data may be filtered using proprietary image filtering methods to provide a controlled version of the data. Further, the data may be analyzed using algorithms and calculations. Further, a therapeutic conclusion is generated to aid in the surgeon's decision making. Further, the data may be stored in a database for future analysis, in an effort to increase understanding of the condition and provide better patient outcomes.

Further, the image interpretation process may take place in two phases. Further, the two phases may include raw image manipulation and data analysis. Further, the raw image manipulation may initiate filtering process, upon uploading the images to the disclosed system. Further, the filtering process may include adjusting brightness, contrast, etc. to identify the veins (common iliac, external iliac, common femoral, etc.) and to detect lumen border. Further, the filtering process may include artificial intelligence analysis for automated detection of the lumen border associated with the veins. Further, the filtering process may include convolutional neural network implementation for automated detection of the lumen border associated with the veins. Further, the filtering process may include simultaneous filtering analysis to determine the best fit line to facilitate lumen area measurements, 3D modeling of veins, identifying maximum and minimum area sites of veins, identifying image slides where these sites occur. Further, the raw image manipulation process may provide information that may be required for data analysis. Further, the data analysis may include analysis of change in blood flow and change in area. Further, the data analysis may include therapeutic decision making that may include recording patient's metrics (such as height, weight, age, area measurements, etc.) and comparing the metrics to the database of patients. Further, the database may find "similar" patients (metrics) with their known outcomes (Patient Outcome Surveys & Any Other Patient Outcome Analysis) and compares them to current patients to perform a confidence analysis. Further, the confidence analysis may generate a numerical value that will allow to perform a second logic test [a numerical test that may set conditional boundaries and appropriate responses to each range of numerical values, Ex: $0<0.25$ (intervene), $0.25\leq0.5$ (Alternative Treatment), $0.5\leq0.75$ (Monitor), $0.75<1$ (Clear)] that may generate a "Best Fit" outcome in the form of what diagnostic steps to take. Further, the therapeutic decision making may include a second data analysis that may be required to perform.

Further, the present disclosure may describe methods and systems that may facilitate treatment of Pelvic Venous Compressions, and specifically May-Thurner Syndrome. Further, May-Thurner Syndrome is a rarely diagnosed condition in which patients may develop deep venous thrombosis (DVT) due to an anatomical variant in which the right common iliac artery overlies and compresses the left common iliac vein against the lumbar spine. further, the treatment of Pelvic Venous Compression disorders may be facilitated by analyzing data through confidence analysis, outlier filtering methods, relative max and min analysis, therapeutic decision making factors, patient database analysis.

Further, the use of artificial intelligence and analysis methods are effective in reducing the number of frames from each set of intravascular images that must be analyzed to effectively determine a value, such as a confluence, cross sectional area, or similar relevant value. In the ideal embodiment, it has been found that the analysis methods and implementation described herein reduce the amount of IVUS frames that must be analyzed to output some analyzed value with confidence is reduce by 5-10% of the total frames that would otherwise need analysis by conventional methods.

FIG. 1 is an illustration of an online platform 100 consistent with various embodiments of the present disclosure. By way of non-limiting example, the online platform 100 to facilitate diagnosing of a central or peripheral vasculature disorder using intravascular imaging may be hosted on a centralized server 102, such as, for example, a cloud computing service. The centralized server 102 may communicate with other network entities, such as, for example, a mobile device 106 (such as a smartphone, a laptop, a tablet computer etc.), other electronic devices 110 (such as desktop computers, server computers etc.), databases 114, and sensors 116 over a communication network 104, such as, but not limited to, the Internet. Further, users of the online platform 100 may include relevant parties such as, but not limited to, end-users, administrators, service providers, service consumers and so on. Accordingly, in some instances, electronic devices operated by the one or more relevant parties may be in communication with the platform.

A user 112, such as the one or more relevant parties, may access online platform 100 through a web based software application or browser. The web based software application may be embodied as, for example, but not be limited to, a website, a web application, a desktop application, and a mobile application compatible with a computing device 900.

Figure 2:
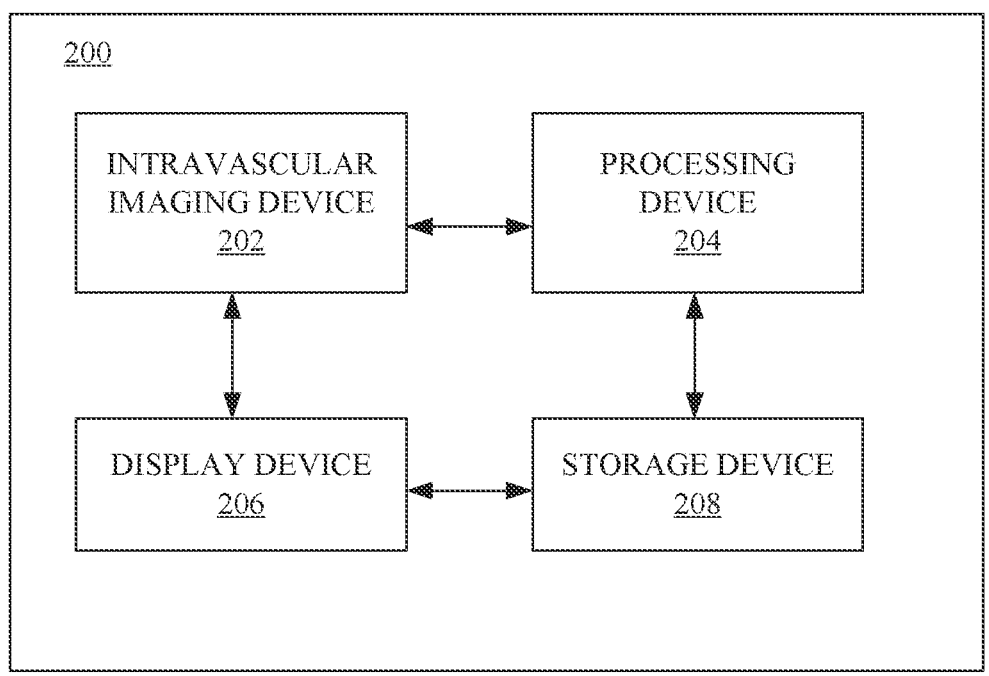
FIG. 2 is a block diagram of a system configured for facilitating diagnosing of a vasculature disorder using intravascular imaging, in accordance with some embodiments.

FIG. 2 is a block diagram of a system 200 configured for facilitating diagnosing of a vasculature disorder using intravascular imaging, in accordance with some embodiments. Accordingly, the system 200 may include an intravascular imaging device 202, a processing device 204, a display device 206 and a storage device 208.

Further, the intravascular imaging device 202 may be configured for generating at least one intravascular image associated with a patient.

Further, the processing device 204 may be communicatively coupled with the intravascular imaging device 202. Further, the processing device 204 may be configured analyzing the at least one intravascular image. Further, the processing device 204 may be configured for determining at least one vein diagnosis based on the analyzing.

Further, the display device 206 may be communicatively coupled with the intravascular imaging device 202. Further, the display device 206 may be configured for displaying the at least one vein diagnosis.

Further, the storage device 208 may be communicatively coupled with the processing device 204. Further, the storage device 208 may be configured for storing the at least one vein diagnosis and the at least one intravascular image associated with the at least one vein diagnosis in a database.

In further embodiments, a communication device may be communicatively coupled with the processing device 204. Further, the communication device may be configured for receiving patient metric data associated with the patient from at least one external device. Further, the processing device 204 may be configured for analyzing the patient metric data. Further determining of the at least one vein diagnosis may be further based on the analyzing of the patient metric data. Patient metric data may include any physiological data, intervention history, demographic information, and venous measurements available in the patient's medical history. Once received by the processing device 204, the patient metric data may be stored in the storage device 208. Patient metric data may later be accessed by the processing unit or artificial intelligence unit for further analysis and processing.

Further, in some embodiments, the at least one vein diagnosis may be associated with at least one vasculature disorder. Further, the at least one vasculature disorder may include a central vasculature disorder and a peripheral vasculature disorder. Further, the at least one vasculature disorder may be associated with at least one of a blockage, a compression, a lesion and a thrombosis of at least one vein.

Further, in some embodiments, the processing device 204 may be configured for identifying at least one vein associated with at least one vasculature disorder based on the analyzing. Further, the processing device 204 may be configured for detecting a lumen border associated with the at least one vein. Further, the processing device 204 may be configured for generating at least one 3D vein model corresponding to the at least one vein based on the detecting. Further, the at least one 3D vein model may be associated with a cross-sectional area and a measure of fluid flow. Further, the determining of the at least one vein diagnosis may be based on the at least one 3D vein model.

Further, in some embodiments, the processing device 204 may be further configured for generating at least one intervention indication based on the at least one vein diagnosis. Further, the display device may be configured for displaying the at least one intervention indication.

Further, in some embodiments, the at least one intervention indication may be associated with an improvement of fluid flow in at least one vein. Further, the improvement of fluid flow in the at least one vein relates to recovering of the at least one vein from at least one vasculature disorder.

Further, in some embodiments, the at least one intervention indication may include a plurality of options. Further, each option of the plurality of options corresponds to a treatment approach for the patient.

In further embodiments, at least one biological sensor may be communicatively coupled with the processing device 204. Further, the at least one biological sensor may be configured for generating at least one patient data associated with the patient. Further, the processing device 204 may be configured for analyzing the at least one patient data. Further, the determining of the at least one vein diagnosis may be further based on the analyzing of the at least one patient data.

Further, in some embodiments, the processing device 204 may be further configured for identifying at least one vasculature disorder based on the least one intravascular image. Further, the storage device may be further configured for retrieving at least one historical patient data based on the identifying. Further, the processing device may be configured for analyzing the at least one historical patient data. Further, the determining of the at least one vein diagnosis may be further based on the analyzing of the at least one historical patient data.

In further embodiments, at least one therapy device may be communicatively coupled with the intravascular imaging device 202. Further, the at least one therapy device may be configured to provide at least one therapy to the patient based on the at least one vein diagnosis.

Figure 3:
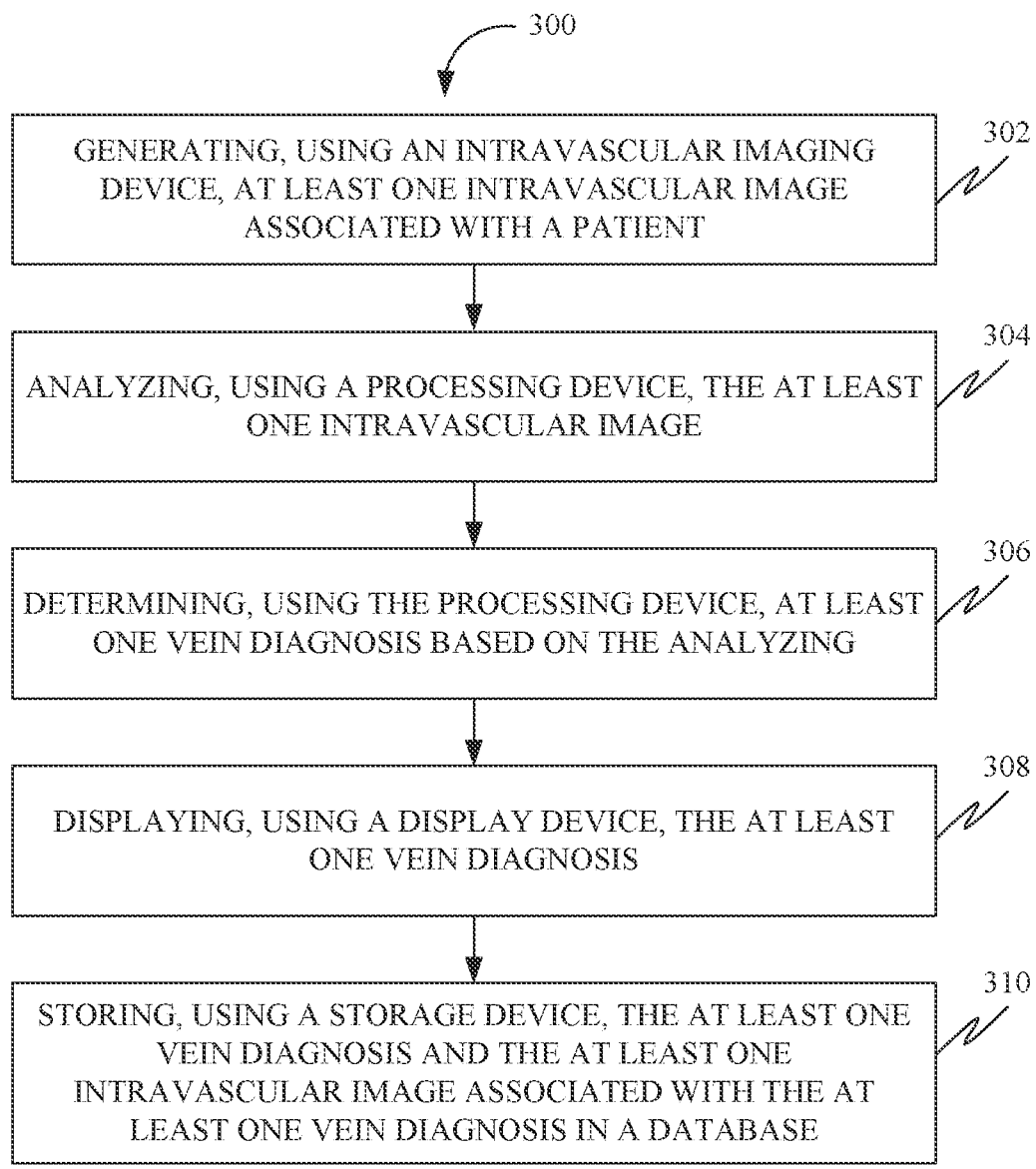
FIG. 3 is a flowchart of a method for facilitating diagnosing of a vasculature disorder using intravascular imaging, in accordance with some embodiments.

FIG. 3 is a flowchart of a method 300 for facilitating diagnosing of a vasculature disorder using intravascular imaging, in accordance with some embodiments. Accordingly, at 302, the method 300 may include a step of generating, using an intravascular imaging device (such as the intravascular imaging device 202), at least one intravascular image associated with a patient.

Further, at 304, the method 300 may include a step of analyzing, using a processing device (such as the processing device 204), the at least one intravascular image.

Further, at 306, the method 300 may include a step of determining, using the processing device, at least one vein diagnosis based on the analyzing. Further, the at least one vein diagnosis may be associated with at least one vasculature disorder. Further, the at least one vasculature disorder may include a central vasculature disorder and a peripheral vasculature disorder. Further, the at least one vasculature disorder may be associated with at least one of a blockage, a compression, a lesion and a thrombosis of at least one vein.

Further, at 308, the method 300 may include a step of displaying, using a display device (such as the display device 206), the at least one vein diagnosis.

Further, at 310, the method 300 may include a step of storing, using a storage device (such as the storage device 208), the at least one vein diagnosis and the at least one intravascular image associated with the at least one vein diagnosis in a database.

In further embodiments, the method 300 may include a step of transmitting, using a communication device, at least one vein diagnosis to at least one therapy device communicatively coupled with the intravascular imaging device. Further, the at least one therapy device may be configured to provide at least one therapy to the patient based on the at least one vein diagnosis.

Figure 4:
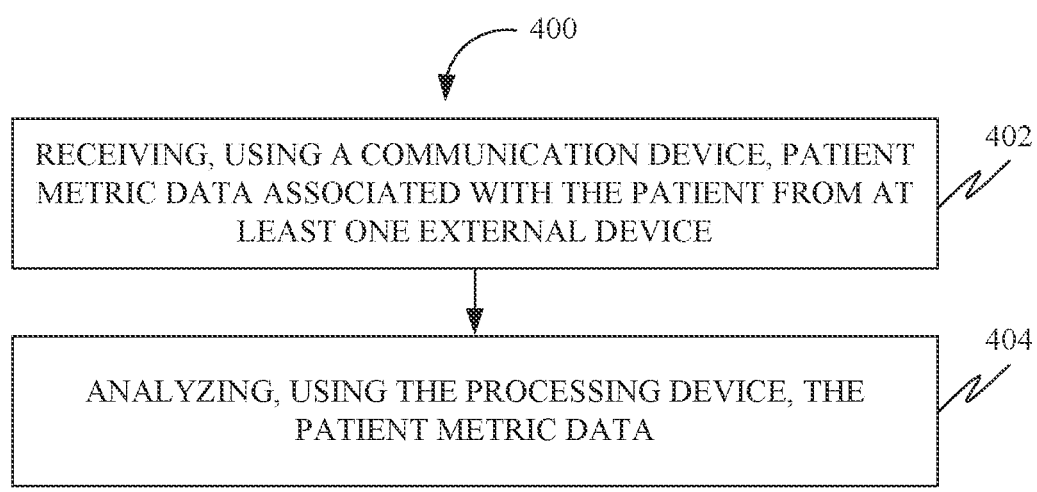
FIG. 4 is a flowchart of a method for facilitating determination of vein diagnosis based on patient metric data, in accordance with some embodiments.

FIG. 4 is a flowchart of a method 400 for facilitating determination of vein diagnosis based on patient metric data, in accordance with some embodiments. Accordingly, at 402, the method 400 may include a step of receiving, using a communication device, patient metric data associated with the patient from at least one external device.

Further, at 404, the method 400 may include a step of analyzing, using the processing device, the patient metric data. Further, the determining of the at least one vein diagnosis may be further based on the analyzing of the patient metric data.

Figure 5:
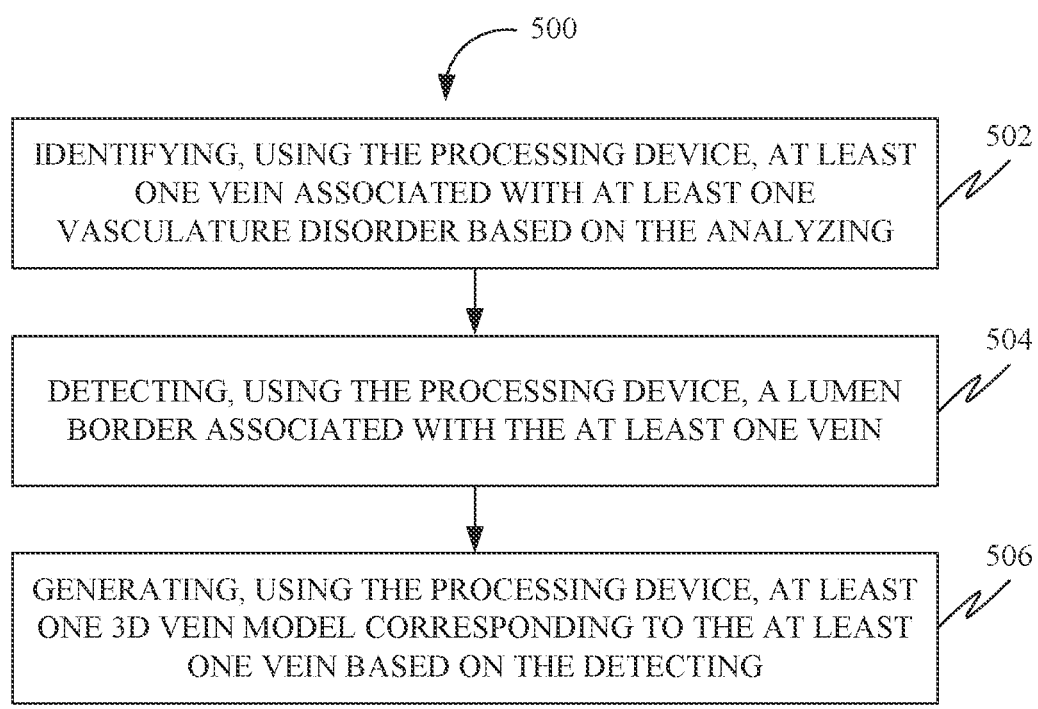
FIG. 5 is a flowchart of a method for facilitating the generation of a 3D vein model corresponding to a vein, in accordance with some embodiments.

FIG. 5 is a flowchart of a method 500 for facilitating the generation of a 3D vein model corresponding to a vein, in accordance with some embodiments. Accordingly, at 502, the method 500 may include a step of identifying, using the processing device, at least one vein associated with at least one vasculature disorder based on the analyzing. Further, the at least one vasculature disorder may include a central vasculature disorder and a peripheral vasculature disorder.

Further, at 504, the method 500 may include a step of detecting, using the processing device, a lumen border associated with the at least one vein. Further, the detecting may include artificial intelligence analysis and convolutional neural network implementation.

Further, at 506, the method 500 may include a step of generating, using the processing device, at least one 3D vein model corresponding to the at least one vein based on the detecting. Further, the at least one 3D vein model may be associated with a cross-sectional area and a measure of fluid flow. Further, the determining of the at least one vein diagnosis may be based on the at least one 3D vein model.

Figure 6:
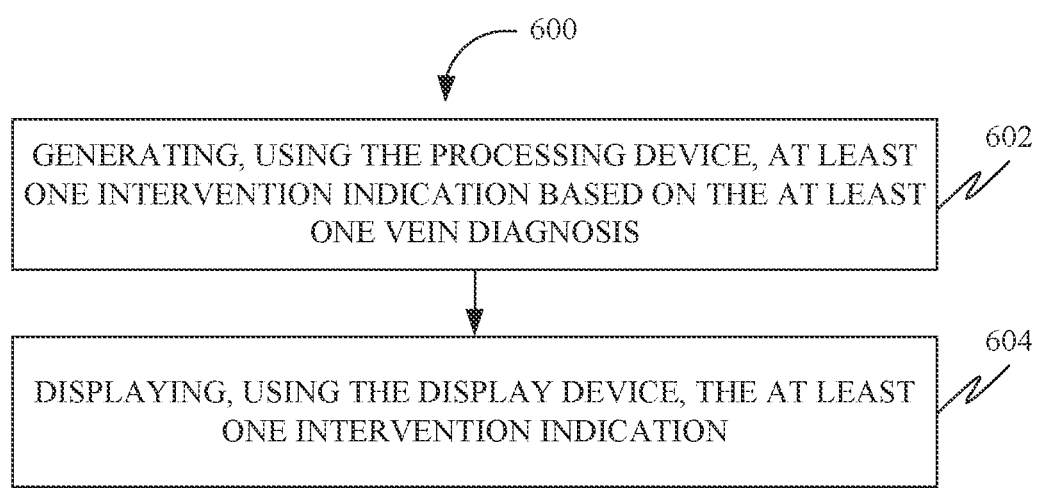
FIG. 6 is a flowchart of a method for facilitating generation and displaying of intervention indication, in accordance with some embodiments.

FIG. 6 is a flowchart of a method 600 for facilitating generation and displaying of intervention indication, in accordance with some embodiments. Accordingly, at 602, the method 600 may include a step of generating, using the processing device, at least one intervention indication based on the at least one vein diagnosis. Further, the at least one intervention indication may be associated with an improvement of fluid flow in at least one vein. Further, the improvement of fluid flow in the at least one vein relates to recovering of the at least one vein from at least one vasculature disorder. Further, the at least one vasculature disorder may include a central vasculature disorder and a peripheral vasculature disorder. Further, the at least one intervention indication may include a plurality of options. Further, each option of the plurality of options corresponds to a treatment approach for the patient Further, at 604, the method 600 may include a step of displaying, using the display device, the at least one intervention indication.

Figure 7:
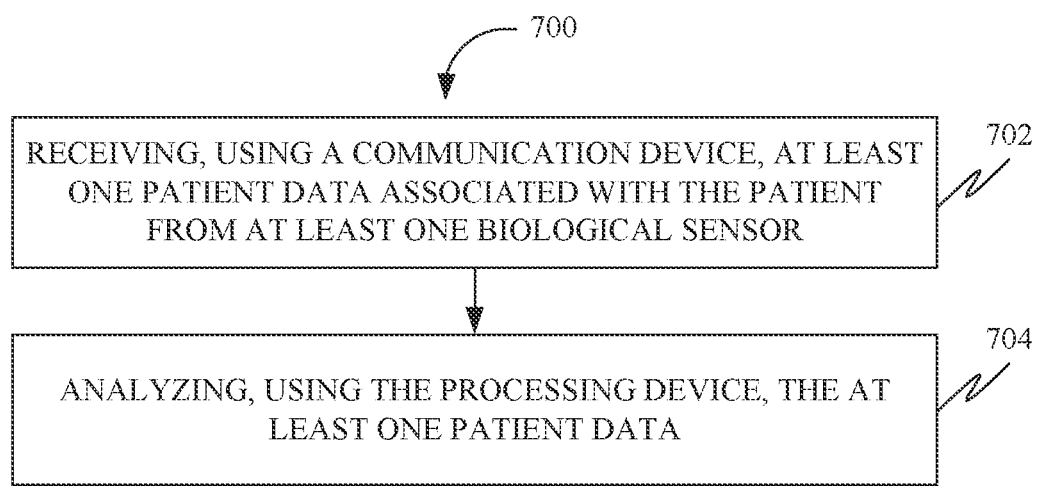
FIG. 7 is a flowchart of a method for facilitating determination of vein diagnosis based on patient data, in accordance with some embodiments.

FIG. 7 is a flowchart of a method 700 for facilitating determination of vein diagnosis based on patient data, in accordance with some embodiments. Accordingly, at 702, the method 700 may include a step of receiving, using a communication device, at least one patient data associated with the patient from at least one biological sensor. Further, the at least one biological sensor may be configured to generate the at least one patient data.

Further, at 704, the method 700 may include a step of analyzing, using the processing device, the at least one patient data. Further, the determining of the at least one vein diagnosis may be further based on the analyzing of the at least one patient data.

Figure 8:
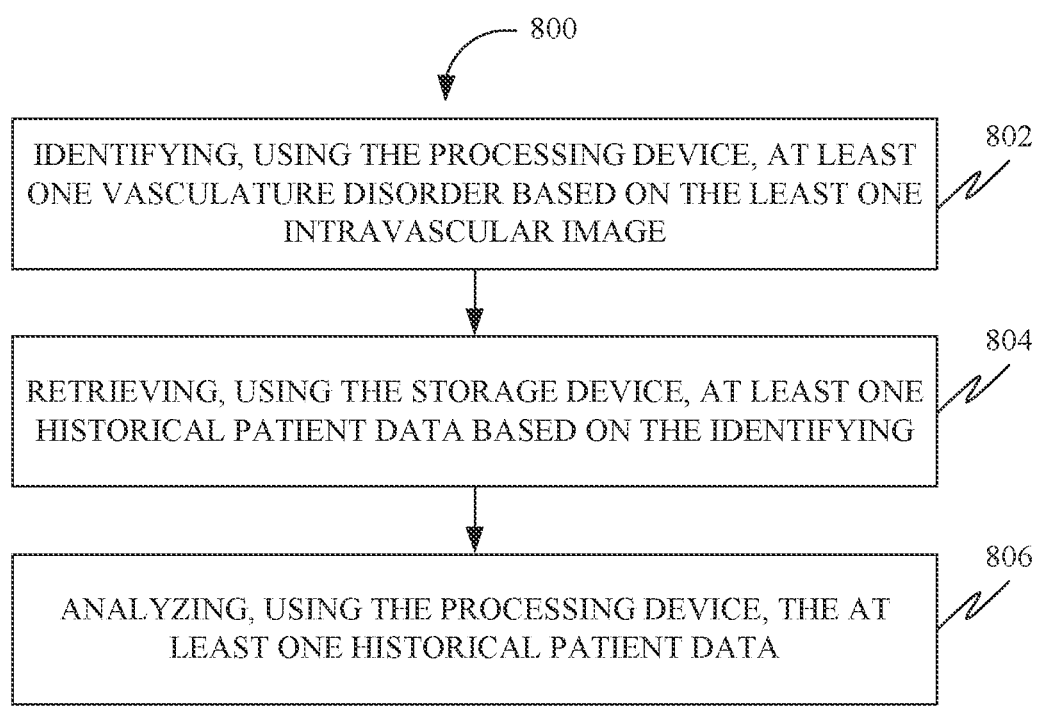
FIG. 8 is a flowchart of a method for facilitating determination of vein diagnosis based on historical patient data, in accordance with some embodiments.

FIG. 8 is a flowchart of a method 800 for facilitating determination of vein diagnosis based on historical patient data, in accordance with some embodiments. Accordingly, at 802, the method 800 may include a step of identifying, using the processing device, at least one vasculature disorder based on the at least one intravascular image.

Further, at 804, the method 800 may include a step of retrieving, using the storage device, at least one historical patient data based on the identifying.

Further, at 806, the method 800 may include a step of analyzing, using the processing device, the at least one historical patient data. Further, the determining of the at least one vein diagnosis may be further based on the analyzing of the at least one historical patient data.

Figure 9:
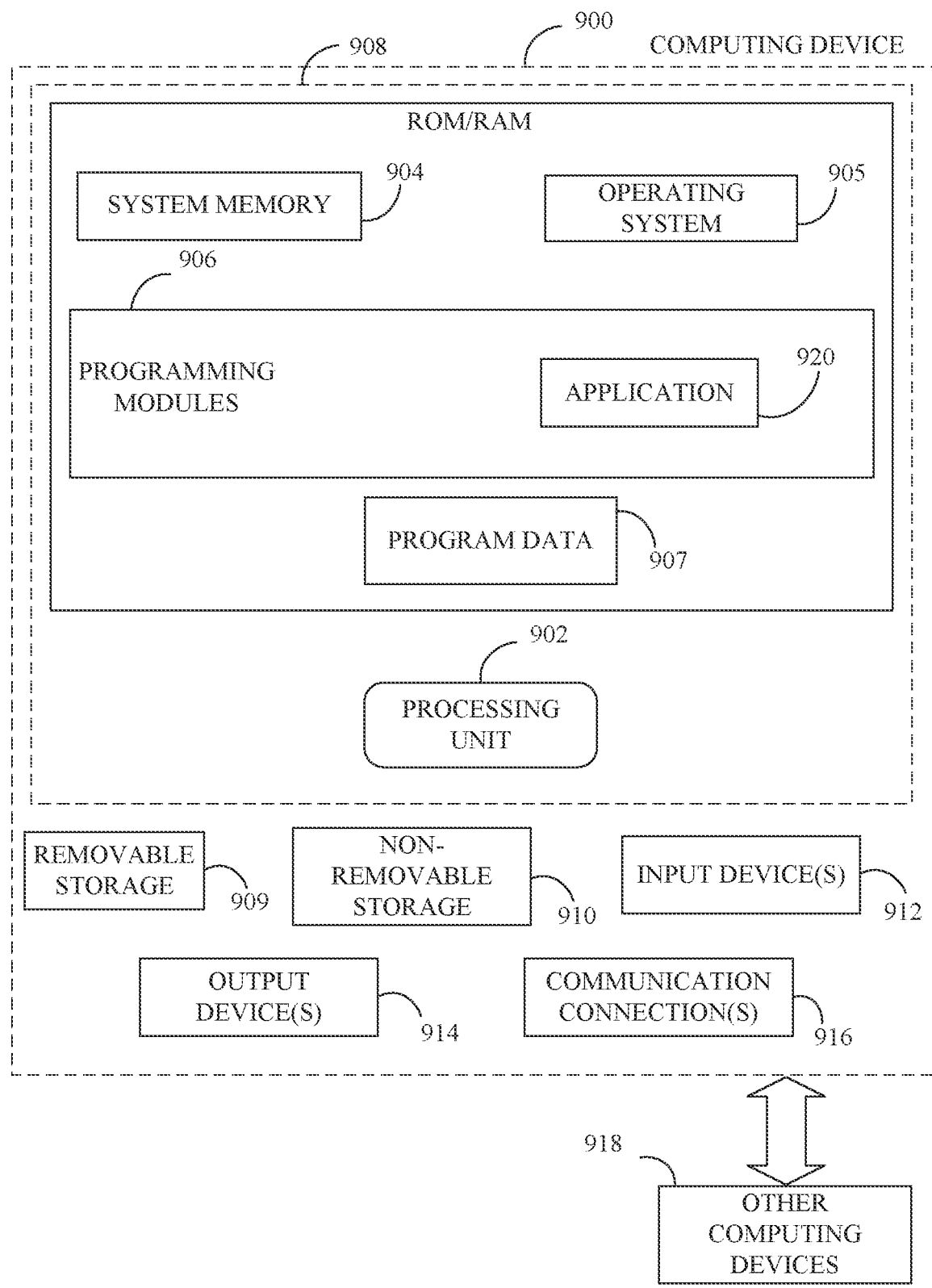
FIG. 9 is a block diagram of a computing device for implementing the methods disclosed herein, in accordance with some embodiments.

With reference to FIG. 9, a system consistent with an embodiment of the disclosure may include a computing device or cloud service, such as computing device 900. In a basic configuration, computing device 900 may include at least one processing unit 902 and a system memory 904. Depending on the configuration and type of computing device, system memory 904 may comprise, but is not limited to, volatile (e.g. random-access memory (RAM)), non-volatile (e.g. read-only memory (ROM)), flash memory, or any combination. System memory 904 may include operating system 905, one or more programming modules 906, and may include a program data 907. Operating system 905, for example, may be suitable for controlling computing device 900's operation. In one embodiment, programming modules 906 may include image-processing module, machine learning module. Furthermore, embodiments of the disclosure may be practiced in conjunction with a graphics library, other operating systems, or any other application program and is not limited to any particular application or system. This basic configuration is illustrated in FIG. 9 by those components within a dashed line 908.

Computing device 900 may have additional features or functionality. For example, computing device 900 may also include additional data storage devices (removable and/or non-removable) such as, for example, magnetic disks, optical disks, or tape. Such additional storage is illustrated in FIG. 9 by a removable storage 909 and a non-removable storage 910. Computer storage media may include volatile and non-volatile, removable and non-removable media implemented in any method or technology for storage of information, such as computer-readable instructions, data structures, program modules, or other data. System memory 904, removable storage 909, and non-removable storage 910 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 900. Any such computer storage media may be part of device 900. Computing device 900 may also have input device(s) 912 such as a keyboard, a mouse, a pen, a sound input device, a touch input device, a location sensor, a camera, a biometric sensor, etc. Output device(s) 914 such as a display, speakers, a printer, etc. may also be included. The aforementioned devices are examples and others may be used.

Computing device 900 may also contain a communication connection 916 that may allow device 900 to communicate with other computing devices 918, such as over a network in a distributed computing environment, for example, an intranet or the Internet. Communication connection 916 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both storage media and communication media.

As stated above, a number of program modules and data files may be stored in system memory 904, including operating system 905. While executing on processing unit 902, programming modules 906 (e.g., application 920 such as a media player) may perform processes including, for example, one or more stages of methods, algorithms, systems, applications, servers, databases as described above. The aforementioned process is an example, and processing unit 902 may perform other processes. Other programming modules that may be used in accordance with embodiments of the present disclosure may include machine learning applications.

In some embodiments, the processing device 204 may further comprise an artificial intelligence unit. In other embodiments, the processing device 204 may be the artificial intelligence unit, and the artificial intelligence unit may perform any functions otherwise performed by the processing device 204. The artificial intelligence unit may comprise any processing unit or computing device that implements any artificial intelligence technology as is known in the art, such as machine learning, a neural network, or other similar artificial intelligence technology.

The artificial intelligence unit may be configured for identifying at least one incomplete area in the at least one intravascular image. For example, a portion of the intravascular image may be obscured by an artifact such as a motion artifact, or a portion of the intravascular image may be missing due to an error during the ultrasound test. The artificial intelligence may be trained to identify the missing portion of the intravascular image. In some embodiments, one or more intravascular images that do not contain any artifacts or missing data may be identified by the processing unit stored in the storage unit or database, these intravascular images being hereinafter referred to as complete intravascular images. These complete intravascular images may then be used to train the artificial intelligence unit to better recognize an intravascular image that may have missing information or artifacts. These complete intravascular images may further be used to train the artificial intelligence unit to reconstruct an intravascular image to repair missing information or remove artifacts from the at least one intravascular image.

In some embodiments, the artificial intelligence unit may be configured to identify a confluence. The confluence may comprise an area where one or more veins connect or overlap. The artificial intelligence unit may be further configured for identifying a region of interest in a confluence of veins based on the at least one intravascular image. The artificial intelligence unit may first be adapted to identify a confluence of veins in one or more intravascular images. For example, the artificial intelligence unit may select at least one image from one or more intravascular image that meet the characteristics of a confluence. Next, the artificial intelligence unit may be adapted to identify a region of interest inside the confluence. A region of interest may be any area with medically significant information that may be desired by a physician or medical personnel, such as the lumen border, the cross sectional area of the lumen border, or other similar information regarding the subject of the intravascular image or other medical image.

The artificial intelligence unit may be further configured for measuring a physiological contribution of a plurality of veins involved in the confluence of veins. A physiological contribute may comprise blood flow, volume, characteristics of blood flow, or other similar data relating to the confluence of veins. In cases where a venous constriction occurs at a confluence, the decision to intervene may be subjective. By assessing the physiological contribution of the plurality of veins involved in the confluence of veins, the artificial intelligence unit may better assess, diagnose, or recommend a course of action or intervention for the patient.

In some embodiments, the artificial intelligence unit may be configured for processing a plurality of intravascular images, ideally to process or identify a value of interest, such as a cross-sectional area or lumen border. In the ideal embodiment, the artificial intelligence unit may first be configured to space each intravascular image by a fraction of the total length of the plurality of intravascular images to create a subset of the plurality of intravascular images. In the ideal embodiment, the artificial intelligence unit may select an image at each 10% of the way through the imaging process from the plurality of intravascular images, though other values are contemplated.

Next, the artificial intelligence unit is configured to analyze the subset of the plurality of intravascular images to create an analysis result. For example, the artificial intelligence unit may be configured to identify a cross sectional area, a lumen border, or any other value of interest for each intravascular image in the subset.

Once each image in the subset has been analyzed, the artificial intelligence unit may be further configured to recursively subdivide the analysis result until a final result is reached. For example, if the artificial intelligence unit is seeking the minimum cross sectional area, the artificial intelligence unit may identify one or more intervals in which a minimum cross sectional area may be present, and repeat the process of analyzing the subset of the interval. For example, if the artificial intelligence unit divides a plurality of intravascular images into ten intervals and identifies a potential minimum cross sectional area in the second interval, the artificial intelligence unit may then subdivide the second interval into another set of ten intervals. The artificial intelligence unit is then configured to repeat this process recursively until a condition is met. The condition may be any condition decided by the user such as identification of a value within a margin of error, or the process may be stopped after a certain number of iterations.

In other embodiments, the analyzing may comprise a search algorithm that is similar to a binary search. First, the analyzing comprises the step of selecting a start frame, a end frame, and a middle frame from a plurality of intravascular images. The middle frame is positioned between the start frame and the end frame, either temporally or physically. A first frame is then selected, the first frame being positioned between the start frame and the middle frame. A second frame is then selected, the second frame being positioned between the middle frame and the end frame. The artificial intelligence unit may then analyze the first frame and the second frame. The analysis may include analyzing each frame to extract a value, such as a cross sectional area, lumen border size, or other similar value or characteristic from the frame. Once the value is extracted, the values in first frame and the second frame are compared, and either the smaller or larger of the two values may be selected. Once selected, the first frame may become the new start frame, and the second frame may become the new end frame. A new middle frame is then generated between the first frame and the second frame, and the analysis repeats. This process repeats until a threshold value is reached. The threshold value may be a number of iterations, a determination that a minimum has been reached based on other factors considered by the artificial intelligence unit, or other condition decided upon by a user. In the ideal embodiment, the above process is used by the artificial intelligence unit to find a minimum cross sectional area from a plurality of IVUS images.

In the ideal embodiment to find a minimal cross sectional area, the start and end frames may be recursively selected as follows to continuously generate new subsets of frames to search. Each time a new start and end frame are selected, a new first and a new second frame are also selected between the new start and end frame as described above, until some threshold value is reached. Once a first frame and second frame are chosen, the values of the first frame and the second frame are compared. If the first frame has a smaller value than the second frame, and the start frame has a smaller value than the second frame: the start and end frame are reselected, with the start frame being the original start frame, and the end frame being the first frame. If the first frame has a smaller value than the second frame and the middle frame has a smaller value than the start frame: the first and second frame are reselected, with the new start frame being the first frame, and the new end frame being the middle frame. If the second frame has a smaller value than the first frame, and the middle frame has a smaller value than the final frame: the start and end frame are reselected, with the middle frame being the new start frame, and the second frame being the new end frame. If the second frame has a smaller value than the first frame, and the final frame has a smaller value than the middle frame: then the start and end frame are reselected, with the second frame being the new start frame, and the final frame being the new end frame. This process then continues, as a new subset of frames is generated by the above. A new first frame and a new second frame are selected from the new subset of frames, and the process repeats until some threshold value is reached. In the ideal embodiment, the process stops when only 10 total frames remain in the new subset. At this point, every remaining frame is searched to determine a minimum.

In some embodiments, the artificial intelligence unit may be configured to merge together a plurality of intravascular images. For example, the artificial intelligence unit may merge together images taken from multiple IVUS scans into a merged intravascular image. Once merged, the artificial intelligence unit may be further configured for merging together the plurality of intravascular images to establish a congregated average. For example, when calculating a cross sectional area, the artificial intelligence unit may be configured to take the mean of the minimum cross sectional area of a vein across the merged intravascular image. This process improves accuracy, especially when applied to the reconstruction of missing data or artifacts in an intravascular image, as described above.

In some embodiments, the database may be further configured for storing at least one intravascular image, the selected intravascular image being ideally selected as being free of artifacts and without any missing data. The database may be communicatively coupled to the artificial intelligence unit, such that the database is configured to repeatedly send any newly received intravascular images to the artificial intelligence unit for processing. Once received, the artificial intelligence unit may use the received intravascular images to train a machine learning model. By training on complete images without artifacts, the artificial intelligence unit may be continuously trained and updated to better reconstruct any intravascular images that have artifacts or are otherwise missing data. In the ideal embodiment, any time a plurality of intravascular images are received, any of those plurality of intravascular images that are free of artifacts or missing data are sent to the artificial intelligence unit to assist with training.

Figure 10:
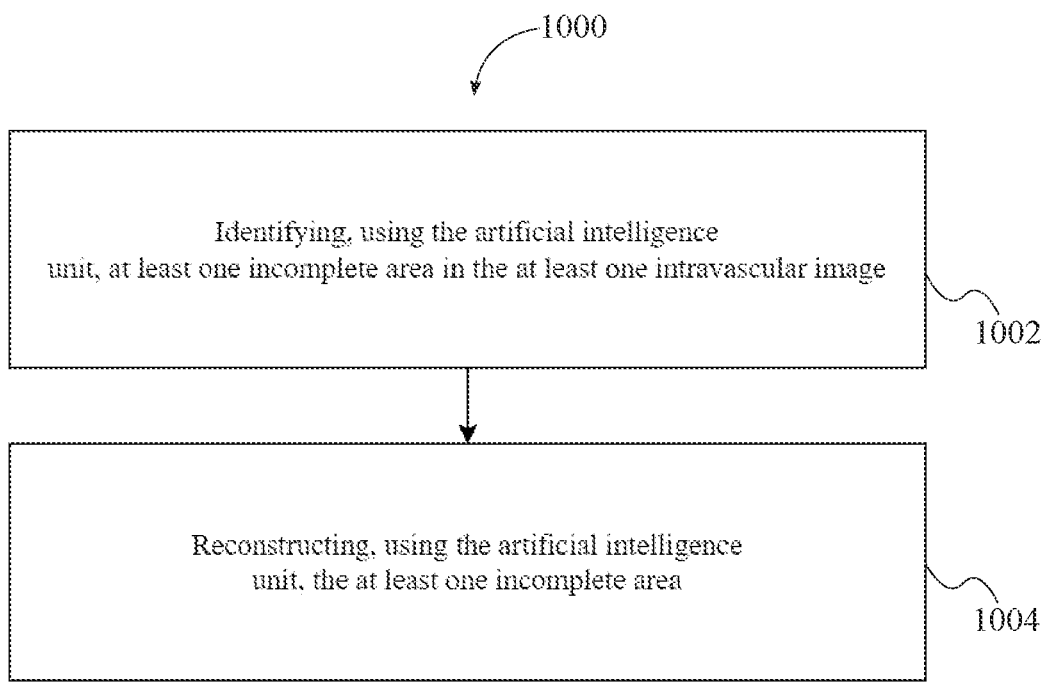
FIG. 10 is a flowchart of a method for identifying and reconstructing incomplete areas in an intravascular image.

As seen in FIG. 10, a method 1000 for repairing medical images is described. At 1002, the method may comprise identifying, using the artificial intelligence unit, at least one incomplete area in the at least one intravascular image. At 1004, the method may comprise reconstructing, using the artificial intelligence unit, the at least one incomplete area.

Figure 11:
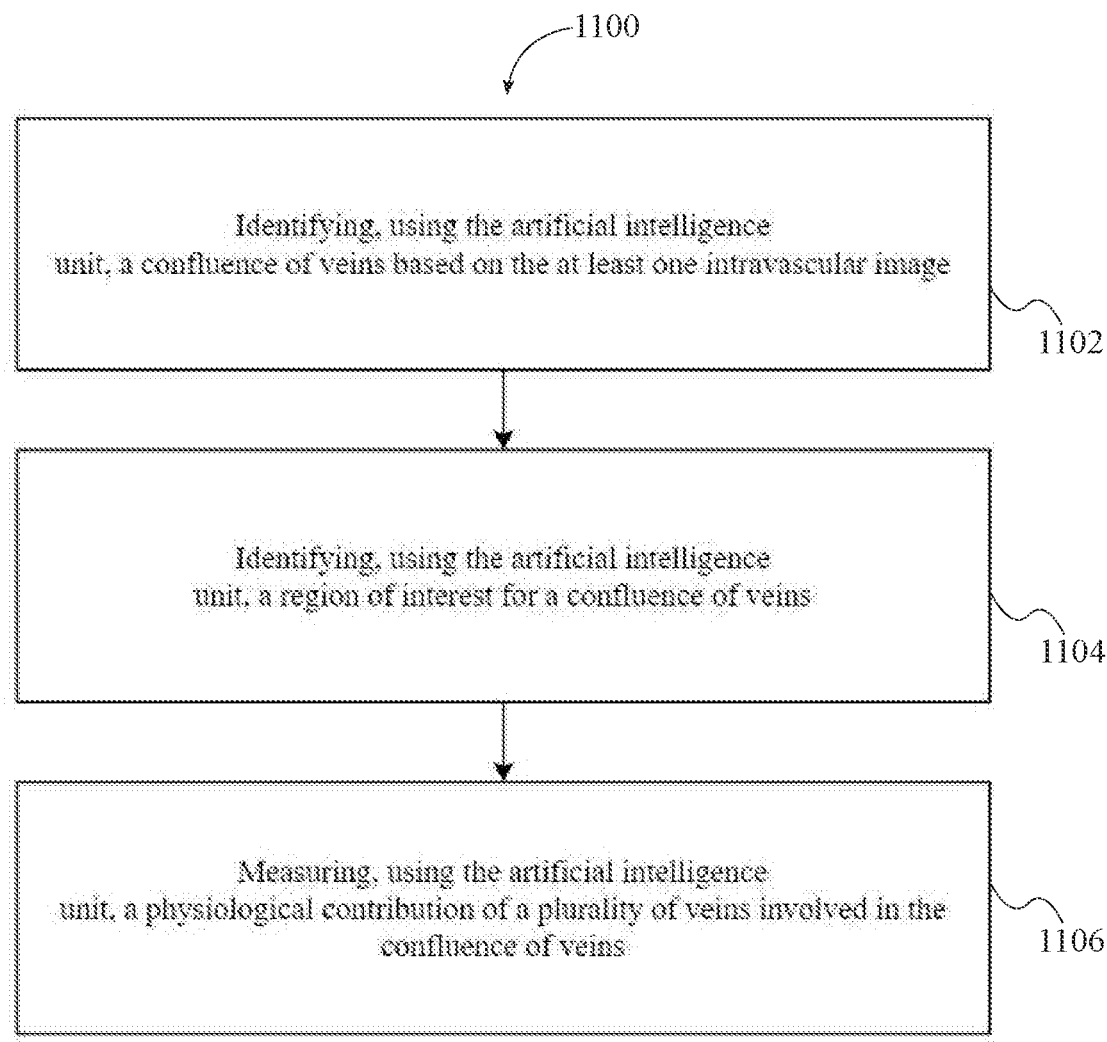
FIG. 11 is a flowchart of a method for identifying a confluence, a region of interest, and measuring a value associated with an intravascular image.
Figure 12:
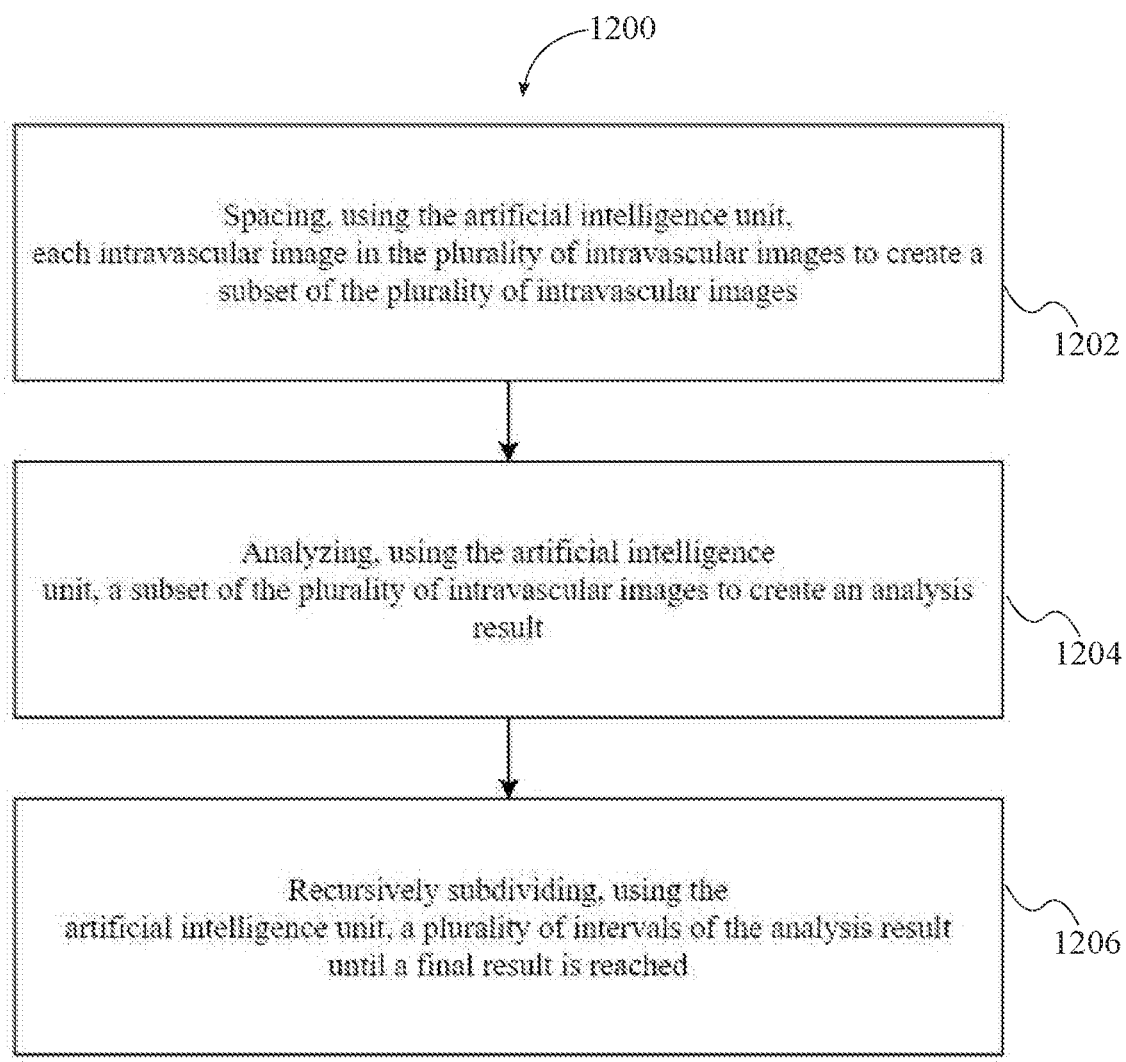
FIG. 12 is a flowchart of a method for analyzing a plurality of intravascular images to obtain a final result.

As seen in FIG. 11, a method 1100 for assessing regions of interest is described. At 1102, the method may comprise identifying, using the artificial intelligence unit, a confluence of veins based on the at least one intravascular image. At 1104, the method may further comprise identifying, using the artificial intelligence unit, a region of interest for a confluence of veins. At 1106, the method may further comprise measuring, using the artificial intelligence unit, a physiological contribution of a plurality of veins involved in the confluence of veins.

For the method 1200, the at least one intravascular image comprising a plurality of intravascular images. At 1202, the method may comprise spacing, using the artificial intelligence unit, each intravascular image in the plurality of intravascular images by a fraction of a total length of the plurality of intravascular images to create a subset of the plurality of intravascular images. At 1204, the method may comprise analyzing, using the artificial intelligence unit, a subset of the plurality of intravascular images to create an analysis result. At 1206, the method may comprise recursively subdividing, using the artificial intelligence unit, a plurality of intervals of the analysis result until a final result is reached.

Figure 13:
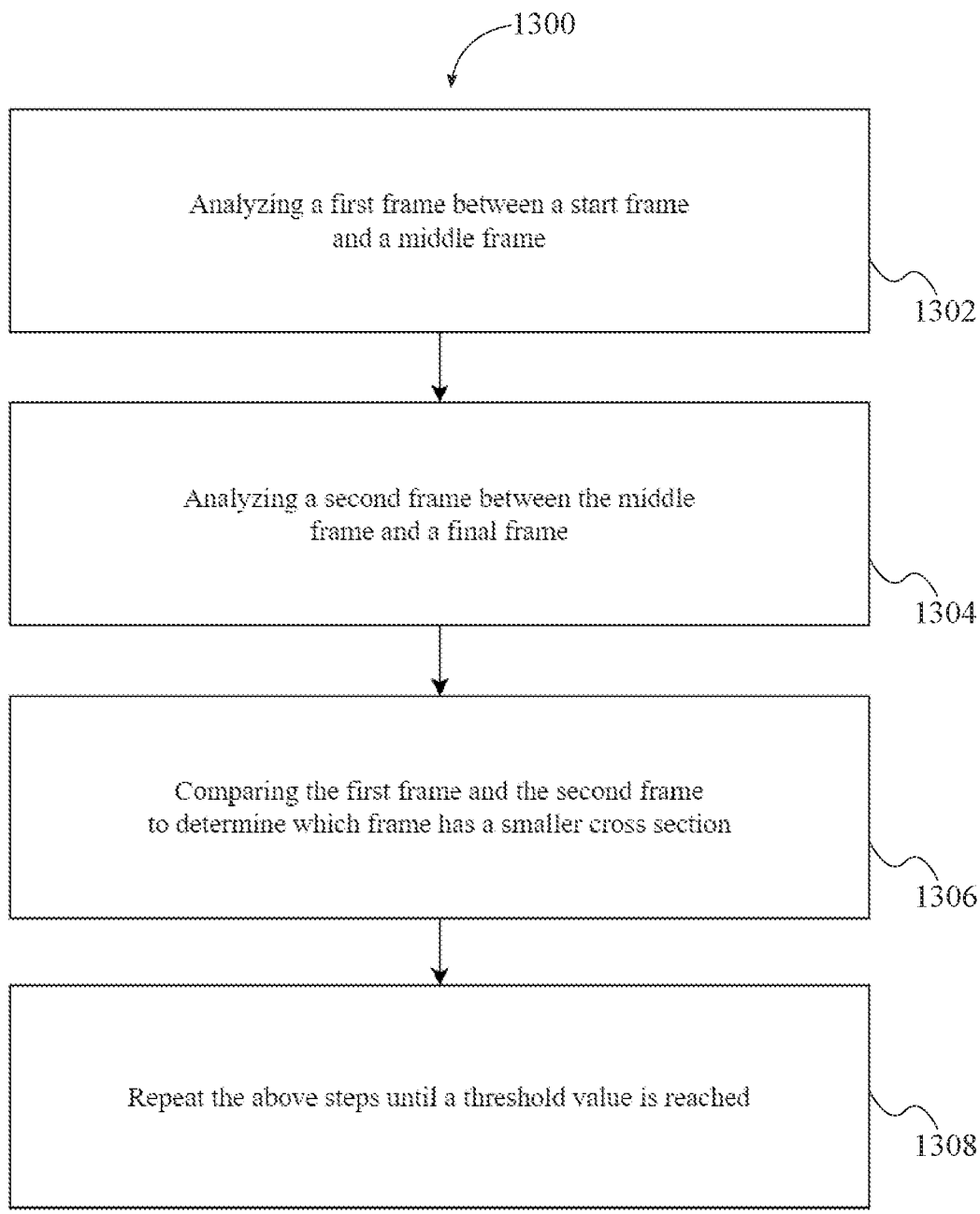
FIG. 13 is a flowchart of a method for analyzing a plurality of intravascular images to obtain a value, the exemplary value shown being a cross sectional area.

As shown in FIG. 13, the analyzing of 1206 is further described as method 1300. The analyzing at 1302 may further comprise analyzing a first frame between a start frame and a middle frame. The method at 1304 may further comprise analyzing a second frame between the middle frame and a final frame. The method at 1306 may further comprise comparing the first frame and the second frame to determine which frame has a smaller cross section. The method at 1306 may further comprise repeating the above steps until a frame with a smallest cross section is found. For example, 1306 may check to see if a threshold value has been reached. If no threshold value is reached, the method may return to 1302. It should be understood that the above method may be applied not just to determining a cross section or cross sectional area, but also to extracting any value which may be based on comparison.

A method of merging multiple intravascular images is described. The method may comprise merging, using the processing device, the plurality of intravascular images to establish a congregated average.

Figure 14:
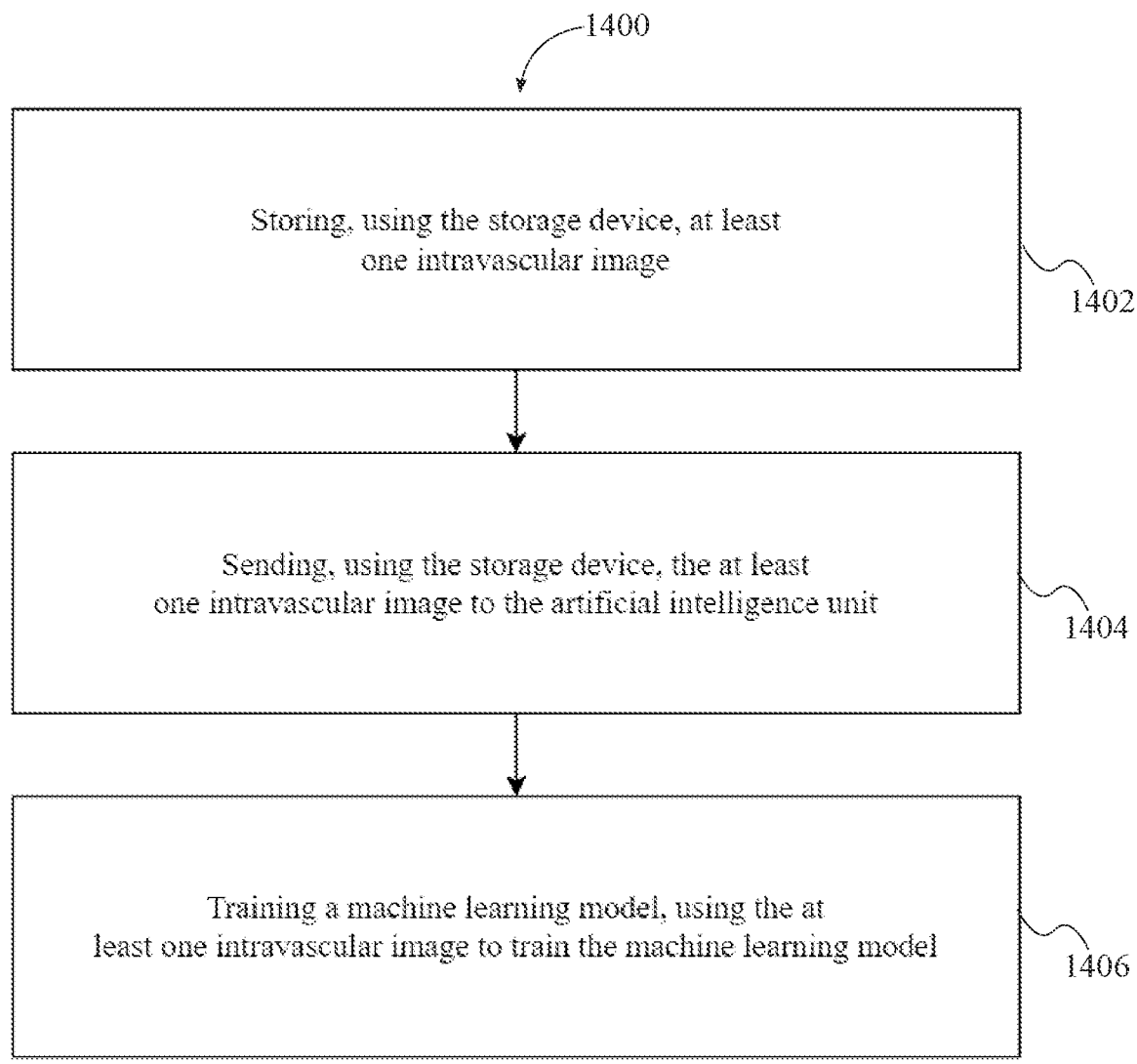
FIG. 14 is a flowchart of a method for training an artificial intelligence unit, the exemplary artificial intelligence unit implementing and training a machine learning model.

As shown in FIG. 14, a method 1400 of training an artificial intelligence unit is described. The method at 1402 may comprise storing, using the storage device, the at least one intravascular image, wherein the at least one intravascular image selected for storage is free of artifacts. The method at 1404 may further comprise sending, using the storage device, the at least one intravascular image to the artificial intelligence unit. The method at 1406 may further comprise training a machine learning model, using the at least one intravascular image to train the machine learning model. Though a machine learning model is described, it should be understood that the above method may be applied to an similar artificial intelligence model, including but not limited to neural networks. In the ideal embodiment, it should be understood that method 1400 is a global process using a global database for storage, such that any IVUS procedure performed anywhere on the globe may be used for training. This configuration allows for a wide variety of IVUS procedures from varied individual backgrounds to be used to rapidly improve the accuracy and efficiency of the artificial intelligence unit.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general purpose graphics processor-based systems, multiprocessor systems, microprocessor-based or programmable consumer electronics, application specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example, but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Although the present disclosure has been explained in relation to its preferred embodiment, it is to be understood that many other possible modifications and variations can be made without departing from the spirit and scope of the disclosure.

What is claimed is:

1. A system for facilitating diagnosing of a vasculature disorder using intravascular imaging, the system comprising:
    an intravascular imaging device configured for generating at least one intravascular image associated with a patient;
    a processing device communicatively coupled with the intravascular imaging device, wherein the processing device is configured for:
        analyzing the at least one intravascular image;
        determining at least one vein diagnosis based on the analyzing;
    the processing device further comprising an artificial intelligence unit;
    a display device communicatively coupled with the intravascular imaging device, wherein the display device is configured for displaying the at least one vein diagnosis;
    a storage device communicatively coupled with the processing device, wherein the storage device is configured for storing the at least one vein diagnosis and the at least one intravascular image associated with the at least one vein diagnosis in a database;
    wherein the storage device is further configured for storing at least one patient demographic information, at least one intervention history, at least one venous measurement, and at least one physiological data in the database;
    wherein the processing device is further configured for identifying at least one vein associated with at least one vasculature disorder based on the analyzing;
    the artificial intelligence unit being configured for:
        identifying at least one incomplete area in the at least one intravascular image;
        reconstructing the at least one incomplete area;
        detecting a lumen border associated with the at least one vein; and
        generating at least one 3D vein model corresponding to the at least one vein based on the detecting, wherein the at least one 3D vein model is associated with a cross-sectional area and a measure of fluid flow, wherein the determining of the at least one vein diagnosis is based on the at least one 3D vein model.

2. The system of claim 1, wherein the processing device is configured for analyzing the patient metric data, wherein determining of the at least one vein diagnosis is further based on the analyzing of the patient metric data.

3. The system of claim 1, wherein the artificial intelligence unit is configured for:
    identifying a confluence of veins based on the at least one intravascular image;
    identifying a region of interest for a confluence of veins; and
    measuring a physiological contribution of a plurality of veins involved in the confluence of veins.

4. The system of claim 1, wherein the processing device is further configured for generating at least one intervention indication based on the at least one vein diagnosis, wherein the display device is configured for displaying the at least one intervention indication.

5. The system of claim 1, further comprising:
    the at least one intravascular image comprising a plurality of intravascular images;
    the artificial intelligence unit being further configured for:
        spacing each intravascular image by a fraction of a total length of the plurality of intravascular images to create a subset of the plurality of intravascular images;
        analyzing a subset of the plurality of intravascular images to create an analysis result; and
        recursively subdividing the analysis result until a final result is reached.

6. The system of claim 5, further comprising:
    wherein the analyzing comprises:
        analyzing a first frame between a start frame and a middle frame;

analyzing a second frame between the middle frame and a final frame;

comparing the first frame and the second frame to determine which frame has a smaller cross sectional area;

repeating the above steps until a threshold condition is met.

7. The system of claim 1, further comprising:

the at least one intravascular image comprising a plurality of intravascular images;

wherein the processing device is further configured for merging together the plurality of intravascular images to establish a congregated average.

8. The system of claim 1, further comprising:

wherein the database is further configured for storing the at least one intravascular image;

wherein the at least one intravascular image selected for storage is free of artifacts;

wherein the database is configured to continuously send the at least one intravascular image to the artificial intelligence unit;

wherein the artificial intelligence unit is configured for using the at least one intravascular image to train a machine learning model.

9. The system of claim 1 further comprising:

at least one biological sensor communicatively coupled with the processing device;

wherein the at least one biological sensor is configured for generating at least one patient data associated with the patient;

wherein the processing device is configured for analyzing the at least one patient data;

wherein the determining of the at least one vein diagnosis is further based on the analyzing of the at least one patient data; and wherein the processing device is further configured for identifying at least one vasculature disorder based on the least one intravascular image, wherein the storage device is further configured for retrieving at least one historical patient data based on the identifying.

10. The system of claim 1, wherein:

the processing device is configured for analyzing the at least one historical patient data, wherein the determining of the at least one vein diagnosis is further based on the analyzing of the at least one historical patient data; and the at least one therapy device being communicatively coupled with the intravascular imaging device, wherein the at least one therapy device is configured to provide at least one therapy to the patient based on the at least one vein diagnosis.

11. A method for facilitating diagnosing of a vasculature disorder using intravascular imaging, the method comprising:

generating, using an intravascular imaging device, at least one intravascular image associated with a patient;

analyzing, using a processing device, the at least one intravascular image;

determining, using the processing device, at least one vein diagnosis based on the analyzing;

displaying, using a display device, the at least one vein diagnosis storing, using a storage device, the at least one vein diagnosis and the at least one intravascular image associated with the at least one vein diagnosis in a database;

storing, using the storage device, at least one patient demographic information, at least one intervention history, at least one venous measurement, and at least one physiological data in the database;

identifying, using the processing device, at least one vein associated with at least one vasculature disorder based on the analyzing;

detecting, using the processing device, a lumen border associated with the at least one vein;

identifying, using an artificial intelligence unit, at least one incomplete area in the at least one intravascular image;

reconstructing, using the artificial intelligence unit, the at least one incomplete area; and generating, using the processing device, at least one 3D vein model corresponding to the at least one vein based on the detecting, wherein the at least one 3D vein model is associated with a cross-sectional area and a measure of fluid flow, wherein the determining of the at least one vein diagnosis is based on the at least one 3D vein model.

12. The method of claim 11 further comprising:

receiving, using a communication device, patient metric data associated with the patient from at least one external device;

analyzing, using the processing device, the patient metric data, wherein determining of the at least one vein diagnosis is further based on the analyzing of the patient metric data.

13. The method of claim 11, further comprising:

identifying, using the artificial intelligence unit, a confluence of veins based on the at least one intravascular image;

identifying, using the artificial intelligence unit, a region of interest for a confluence of veins; and measuring, using the artificial intelligence unit, a physiological contribution of a plurality of veins involved in the confluence of veins.

14. The method of claim 11 further comprising:

generating, using the processing device, at least one intervention indication based on the at least one vein diagnosis;

displaying, using the display device, the at least one intervention indication.

15. The method of claim 11, further comprising:

the at least one intravascular image comprising a plurality of intravascular images;

spacing, using the artificial intelligence unit, each intravascular image by a fraction of a total length of the plurality of intravascular images to create a subset of the plurality of intravascular images;

analyzing, using the artificial intelligence unit, a subset of the plurality of intravascular images to create an analysis result; and recursively subdividing, using the artificial intelligence unit, a plurality of intervals of the analysis result until a final result is reached.

16. The system of claim 15, further comprising:

wherein the analyzing, using the artificial intelligence unit, further comprises:

analyzing a first frame between a start frame and a middle frame;

analyzing a second frame between the middle frame and a final frame;

comparing the first frame and the second frame to determine which frame has a smaller cross section;

repeating the above steps until a frame with a smallest cross section is found.

17. The method of claim 11, further comprising:
the at least one intravascular image comprising a plurality of intravascular images;
merging, using the processing device, the plurality of intravascular images to establish a congregated average.

18. The method of claim 11, further comprising:
storing, using the storage device, the at least one intravascular image, wherein the at least one intravascular image selected for storage is free of artifacts;
sending, using the storage device, the at least one intravascular image to the artificial intelligence unit; and
training a machine learning model, using the at least one intravascular image to train the machine learning model.

19. The method of claim 11 further comprising:
receiving, using a communication device, at least one patient data associated with the patient from at least one biological sensor, wherein the at least one biological sensor is configured to generate the at least one patient data;
analyzing, using the processing device, the at least one patient data, wherein the determining of the at least one vein diagnosis is further based on the analyzing of the at least one patient data.

20. The method of claim 11 further comprising:
identifying, using the processing device, at least one vasculature disorder based on the least one intravascular image;
retrieving, using the storage device, at least one historical patient data based on the identifying;
analyzing, using the processing device, the at least one historical patient data, wherein the determining of the at least one vein diagnosis is further based on the analyzing of the at least one historical patient data; and
transmitting, using a communication device, the at least one vein diagnosis to at least one therapy device communicatively coupled with the intravascular imaging device, wherein the at least one therapy device is configured to provide at least one therapy to the patient based on the at least one vein diagnosis.

* * * * *